US012653769B2

(12) United States Patent
Stebbins et al.

(10) Patent No.: US 12,653,769 B2
(45) Date of Patent: Jun. 16, 2026

(54) ENHANCING PHOTOSTABILITY OF THIOPYRIDINONE COMPOUND WITHOUT THE USE OF UV FILTERS

(71) Applicant: L'OREAL, Paris (FR)

(72) Inventors: Nicholas David Stebbins, Rahway, NJ (US); David Chan, Oradell, NJ (US)

(73) Assignee: L'OREAL, Paris (FR)

( * ) Notice: Subject to any disclaimer, the term of this patent is extended or adjusted under 35 U.S.C. 154(b) by 185 days.

(21) Appl. No.: 17/844,934

(22) Filed: Jun. 21, 2022

(65) Prior Publication Data

US 2023/0404879 A1 Dec. 21, 2023

(51) Int. Cl.
*A61K 8/49* (2006.01)
*A61K 8/42* (2006.01)
*A61Q 19/02* (2006.01)

(52) U.S. Cl.
CPC .............. *A61K 8/4933* (2013.01); *A61K 8/42* (2013.01); *A61K 8/4926* (2013.01); *A61Q 19/02* (2013.01)

(58) Field of Classification Search
None
See application file for complete search history.

(56) References Cited

U.S. PATENT DOCUMENTS

| | | | |
|---|---|---|---|
| 7,150,876 B2 | 12/2006 | Chaudhuri et al. | |
| 2015/0023895 A1* | 1/2015 | Finley ................... | A61Q 17/04 424/59 |

FOREIGN PATENT DOCUMENTS

| | | | | |
|---|---|---|---|---|
| EP | 3390363 B1 * | 9/2019 | .......... | A61K 8/4933 |
| KR | 20160112721 A | 9/2016 | | |
| WO | 2012080075 A1 | 6/2012 | | |
| WO | WO 2017/102349 * | 6/2017 | .......... | C07D 213/82 |
| WO | 2022138471 A1 | 6/2022 | | |

OTHER PUBLICATIONS

DrugBank Online, "Ethylhexyl methoxycrylene", captured Oct. 27, 2020 by The Wayback Machine, https://web.archive.org/web/20201027042007/https://go.drugbank.com/drugs/DB11226 (Year: 2020).*
Dermatology Consultants of Frisco, "Tips for Balancing Your Skin's PH", Dec. 6, 2019, https://mydermconsult.com/blog/tips-for-balancing-your-skins-ph/#:~:text=Use%20pH%2DFriendly%20Products,harsh%20%26%20abrasive%20for%20daily%20use. (Year: 2019).*
Sanadi et al (J Oral and Maxillofacial Pathol 24:374-382, 2020) (Year: 2020).*
Derwent Accession No. 2016-63007L (English summary of Hoon et al (KR 2016-112721A)) (Year: 2016).*
Search Report from corresponding French application FR2211487 mailed May 22, 2023, 9 pages.

* cited by examiner

*Primary Examiner* — Craig D Ricci
(74) *Attorney, Agent, or Firm* — Laetitia Leproust; Robert Klemz

(57) ABSTRACT

The instant disclosure relates to cosmetic compositions and methods of using the cosmetic compositions to benefit the skin. The cosmetic compositions typically include: (a) compounds of thiopyridinone type; (b) and one or more UV boosters. The compositions provide multiple benefits to skin. For example, the compositions are particularly useful for whitening the skin, and for improving skin's appearance.

14 Claims, No Drawings

ENHANCING PHOTOSTABILITY OF THIOPYRIDINONE COMPOUND WITHOUT THE USE OF UV FILTERS

FIELD OF THE DISCLOSURE

Cosmetic compositions providing enhanced photostability of compounds of Thiopyridinone type without the use of UV filters along with methods of use related thereto.

BACKGROUND OF THE DISCLOSURE

It has always been an ultimate target of the cosmetic filed to deliver products with skin benefits such as hydration, moisturizing, anti-aging, whitening, cleansing, and so on. Whitening and brightening of the skin is always high interest of the consumers, especially those who have a dark or dull skin tone. Unfortunately, at various periods of their life, some people see the appearance on their skin, and more in particular on the hands, of darker and/or more colored spots, which give the skin heterogeneity. These spots are in particular due to a high concentration of melanin in the keratinocytes located at the surface of the skin.

Accordingly, there is a need in the art for cosmetic composition that offers stable formulation that includes actives for improving skin smoothness and radiance, brightening skin, dark spots, or a combination of these.

It has always been an ultimate target of the cosmetic filed to deliver products with skin benefits such as hydration, moisturizing, whitening, cleansing, and so on. Whitening and brightening of the skin is always high interest of the consumers, especially those who have a dark or dull skin tone. Unfortunately, at various periods of their life, some people see the appearance on their skin, and more in particular on the hands, of darker and/or more colored spots, which give the skin heterogeneity. These spots are in particular due to a high concentration of melanin in the keratinocytes located at the surface of the skin.

It is known that certain thiopyridinone compounds exhibit good depigmenting activity, even at low concentration, see for example WO2012080075 and WO2017/102349. The thiopyridinone compound can show strong depigmenting or whitening effects by reducing the production of melanin.

SUMMARY OF THE DISCLOSURE

The instant disclosure relates to cosmetic compositions and methods of using the compositions to benefit skin. The compositions improve the appearance of skin. The compositions are unique in their ability to photostabilize compounds of thiopyridinone type. The inventors surprisingly found that the association between Ethylhexyl methoxycrylene and Diethyl Syringylidenemalonate; unexpectedly improves the photostability of compounds of thiopyridinone type (I) or (I'). The instant disclosure minimizes the degradation of compounds of thiopyridinone type when exposed to light and gives the ability to photostabilize compounds of thiopyridinone type without the use of UV filters.

The compositions of the instant disclosure typically include:

i) at least one compound selected from compounds of formula (I) and tautomer of formula (I') herein below; and their optical isomers, racemates, and/or solvates such as hydrates alone or as a mixture:

(I)

(I')

In which Formulas (I) and (I'):

$R_1$ denotes a radical chosen from:
- a) a hydrogen atom;
- b) a saturated linear $C_1$-$C_{10}$ or branched $C_3$-$C_{10}$ alkyl group optionally substituted with one or more groups, which may be identical or different, chosen from:
    - i) —O—$R_3$
    - ii) —S—$R_3$;

$R_2$ denotes a radical chosen from:
- a) a hydrogen atom;
- b) a saturated hydrocarbonated group linear $C_1$-$C_{12}$ or branched $C_3$-$C_{12}$ or cyclic $C_3$-$C_8$, optionally substituted with one or more groups, which may be identical or different, chosen from:
    - i) —O—$R_3$
    - ii) —S—$R_3$
    - iii) —C(O)—O—$R_3$;
    - iv) a $C_5$-$C_{12}$ aryl group optionally substituted with one or more hydroxyls and/or with one or more $C_1$-$C_8$ alkoxy radicals;
- c) a $C_5$-$C_{12}$ aryl group optionally substituted with one or more hydroxyls and/or with one or more $C_1$-$C_8$ alkoxy radicals $R_3$ denotes a radical chosen from:
- a) a hydrogen atom;
- b) a saturated linear $C_1$-$C_{10}$ or branched $C_3$-$C_{10}$ alkyl group;

ii) one or more UV boosters; and wherein the association of one or more UV boosters improves the photostability of compounds of thiopyridinone type.

In some instances, the one or more UV boosters is selected from Ethylhexylmethoxycrylene, Diethyl Syringylidenemalonate and a mixture thereof. In some instances, the one or more UV boosters are present from about 0.01 to about 10 wt. %, based on the total weight of the cosmetic composition.

In some instances, the compound of thiopyridone types is present from about 0.01 to about 10 wt. %, based on the total weight of the cosmetic composition. In some instances, the thiopyridone compound is present from about 0.1 to about 5 wt. %, based on the total weight of the cosmetic composition. In one embodiment, the thiopyridinone compound is present from about 0.5 to about 3 wt. %, based on the total weight of the cosmetic composition.

In some embodiments, Ethylhexyl methoxycrylene is present from about 0.2 to about 3 wt. %, based on the total weight of the cosmetic composition. In various embodiments, Ethylehexyl methoxycrylene is present from about 0.3 to about 2.8 wt. %, based on the total weight of the cosmetic composition.

In some embodiments, Diethyl Syringylidenemalonate is present from about 0.2 to about 3 wt. %, based on the total weight of the cosmetic composition.

In one or more embodiments, the cosmetic composition may have a pH ranging from about 4.5 to about 6.5, preferably from about 5 to about 6.

As mentioned above, the compositions are unique in their ability to photostabilize compounds of thiopyridinone type without the use of UV filters. Accordingly, in some aspects, the instant disclosure relates to methods for photostabilizing compounds of thiopyridinone type with one or more UV boosters comprising combining the compounds of thiopyridinone type with one or more UV boosters, thereby improving the photostability of the compounds of thiopyridinone type.

Finally, the instant disclosure relates to methods of using the compositions described herein, for example, in the treatment of skin. The instant disclosure relates to methods of treating the skin comprising application of the cosmetic composition of the instant disclosure to the skin. The compositions may be used in methods for: depigmenting, lightening and bleaching the keratin materials as well as improving the appearance of skin.

These and other aspects of the disclosure are set out in the appended claims and described in greater detail in the detailed description of the disclosure.

This disclosure describes exemplary embodiments in accordance with the general inventive concepts and is not intended to limit the scope of the disclosure in any way. Indeed, the disclosure as described in the specification is broader than and unlimited by the exemplary embodiments set forth herein, and the terms used herein have their full ordinary meaning.

DETAILED DESCRIPTION OF THE DISCLOSURE

The present disclosure relates to cosmetic compositions typically including at least one compound corresponding to the following formula (I) or (I'), referred to as "compound of thiopyridinone type".

The instant disclosure relates to cosmetic compositions and methods of using the compositions to benefit skin. The compositions improve the appearance of skin. The compositions are unique in their ability to photostabilize Thiopyridinone compounds. The inventors surprisingly found that the association between Ethylehexyl methoxycrylene and Diethyl Syringylidenemalonate; unexpectedly improves the photostability of Thiopyridinone compounds. The instant disclosure improves the stability of Thiopyridinone compounds when exposed to light and gives the ability to photostabilize Thiopyridinone compound without the use of UV filters.

The compositions of the instant disclosure typically include:

i) at least one compound selected from compounds of formula (I) and tautomer of formula (I') herein below; and their optical isomers, racemates, and/or solvates such as hydrates, alone or as a mixture:

In which Formulas (I) and (I'):

R$_1$ denotes a radical chosen from:
- a) a hydrogen atom;
- b) a saturated linear C$_1$-C$_{10}$ or branched C$_3$-C$_{10}$ alkyl group optionally substituted with one or more groups, which may be identical or different, chosen from:
  - i) —O—R$_3$
  - ii) —S—R$_3$;

R$_2$ denotes a radical chosen from:
- a) a hydrogen atom;
- b) a saturated hydrocarbonated group linear C$_1$-C$_{12}$ or branched C$_3$-C$_{12}$ or cyclic C$_3$-C$_8$, optionally substituted with one or more groups, which may be identical or different, chosen from:
  - i) —O—R$_3$
  - ii) —S—R$_3$
  - iii) —C(O)—O—R$_3$;
  - iv) a C$_5$-C$_{12}$ aryl group optionally substituted with one or more hydroxyls and/or with one or more C$_1$-C$_8$ alkoxy radicals;
- c) a C$_5$-C$_{12}$ aryl group optionally substituted with one or more hydroxyls and/or with one or more C$_1$-C$_8$ alkoxy radicals R$_3$ denotes a radical chosen from:
- a) a hydrogen atom;
- b) a saturated linear C$_1$-C$_{10}$ or branched C$_3$-C$_{10}$ alkyl group;

ii) one or more UV boosters; and
wherein the association of one or more UV boosters improves the photostability of compounds of thiopyridinone.

Compounds of Thiopyridinone Type

For the purposes of the instant disclosure, and unless otherwise indicated:

a "saturated hydrocarbonated group linear C$_1$-C$_{12}$ or branched C$_3$-C$_{12}$" is equivalent to a "linear (C$_1$-C$_{12}$) alkyl or branched (C$_3$-C$_{12}$)alkyl group" which correspond to a saturated C$_1$-C$_{12}$ linear or branched C$_3$-C$_{12}$ hydrocarbon based group, and preferably C$_1$-C$_{10}$ linear or C$_3$-C$_{10}$ branched hydrocarbon based group, more preferably C$_1$-C$_6$ linear or C$_3$-C$_6$ branched hydrocarbon-based; Preferentially, the linear or branched groups may be chosen from methyl, ethyl, propyl, isopropyl, butyl, isobutyl and tert-butyl, pentyl, hexyl, heptyl, octyl, nonyl and decyl.

More preferentially, the saturated linear or branched alkyl groups may be chosen from methyl, ethyl, propyl, isopropyl, butyl, isobutyl and tert-butyl, pentyl, hexyl, heptyl and octyl, such as methyl, ethyl, n-pentyl, n-nonyl, isobutyl.

a saturated hydrocarbonated cyclic $C_3$-$C_8$ group is a mono or bicyclic cycloalkyl group containing from 3 to 8 carbon atoms especially is a monocyclic cycloalkyl group in $C_5$ to $C_7$ such as cyclohexyl group, an "alkoxy radical" is an alkyl-oxy radical for which the alkyl radical is a linear or branched $C_1$-$C_{16}$ and preferentially $C_1$-$C_8$ hydrocarbon-based radical;

when the alkoxy group is optionally substituted, this implies that the alkyl group is optionally substituted as defined hereinabove;

an "aryl" group represents a fused or non-fused monocyclic or bicyclic carbon-based group comprising from 5 to 12 carbon atoms, preferably from 6 to 10 carbon atoms, and in which at least one ring is aromatic; preferentially, the aryl radical is a phenyl, biphenyl, naphthyl, more preferably a phenyl group;

the term "at least one" is equivalent to the term "one or more"; and the term "inclusive" for a range of concentrations means that the limits of that range are included in the defined range.

The salts of the compounds of formula (I), (I'), (II) or (II') as defined herein after comprise the conventional non-toxic salts of said compounds, such as those formed from organic or inorganic acid or from organic or inorganic base.

As salts of the compounds of formula (I), (I'), (II) or (II') mention may be made of: the salts obtained by addition of the compound of formula (I) or (II) to:

a mineral base, such as sodium hydroxide, potassium hydroxide, calcium hydroxide, ammonium hydroxide, magnesium hydroxide, lithium hydroxide, and sodium, potassium or calcium carbonate or hydrogen carbonate for example;

or an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made in particular of 2-amino-2-methylpropanol, ethanolamine, triethanolamine, 2-dimethylaminopropanol, 2-amino-2-(hydroxymethyl)-1,3-propanediol and 3-(dimethylamino) propylamine.

Mention may also be made of the salts of amino acids, for instance lysine, arginine, guanidine, glutamic acid and aspartic acid. Advantageously, the salts of the compounds of formula (I) or (II) (when it comprises a carboxy group) may be chosen from alkali metal or alkaline-earth metal salts such as sodium, potassium, calcium or magnesium salts and ammonium salts.

as "organic or inorganic acid salt" is more particularly chosen from salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii)

acetic acid $CH_3C(O)OH$; xiv) triflic acid $CF_3SO_3H$; and xv) tetrafluoroboric acid $HBF_4$;

The acceptable solvates of the compounds described in the instant disclosure comprise conventional solvates such as those formed during the preparation of said compounds owing to the presence of solvents. Mention may be made, by way of example, of the solvates due to the presence of water or of linear or branched alcohols, such as ethanol or isopropanol.

The optical isomers are in particular, the enantiomers and the diastereoisomers.

The compounds used according to the instant disclosure therefore correspond to formula (I) or tautomer (I') below or their salts, their optical isomers, racemates, and/or solvates such as hydrates and the thereof, alone or as a mixture.

In which Formulas (I) and (I'):

$R_1$ denotes a radical chosen from:

a) a hydrogen atom;

b) a saturated linear $C_1$-$C_{10}$ or branched $C_3$-$C_{10}$ alkyl group optionally substituted with one or more groups, which may be identical or different, chosen from:

i) —O—$R_3$ ii) —S—$R_3$;

$R_2$ denotes a radical chosen from:

a) a hydrogen atom;

b) a saturated hydrocarbonated group linear $C_1$-$C_{12}$ or branched $C_3$-$C_{12}$ or cyclic $C_3$-$C_8$, optionally substituted with one or more groups, which may be identical or different, chosen from:

i) —O—$R_3$ ii) —S—$R_3$ iii) —C(O)—O—$R_3$;

iv) a $C_5$-$C_{12}$ aryl group optionally substituted with one or more hydroxyls and/or with one or more $C_1$-$C_8$ alkoxy radicals;

c) a $C_5$-$C_{12}$ aryl group optionally substituted with one or more hydroxyls and/or with one or more $C_1$-$C_8$ alkoxy radicals $R_3$ denotes a radical chosen from:

a) a hydrogen atom;

b) a saturated linear $C_1$-$C_{10}$ or branched $C_3$-$C_{10}$ alkyl group;

The compound (I') is the tautomer form of the compound (I) when a tautomeric equilibrium exists according to the following scheme:

(I)             (I')

According to one embodiment of the disclosure $R_1$ represents one hydrogen atom.

According to another embodiment of the disclosure $R_1$ represents a linear $(C_1\text{-}C_{10})$alkyl group or branched $(C_3\text{-}C_{10})$alkyl group, especially a linear $(C_1\text{-}C_6)$alkyl group or branched $(C_3\text{-}C_6)$alkyl group, such as methyl, ethyl, n-pentyl, n-nonyl, isobutyl, more preferably ethyl. Particularly the said alkyl group of $R_1$ is not substituted.

According to one embodiment of the disclosure $R_2$ represents one hydrogen atom.

According to another embodiment of the disclosure $R_2$ represents a linear $(C_1\text{-}C_{10})$alkyl group or branched $(C_3\text{-}C_{10})$alkyl group, especially a linear $(C_1\text{-}C_6)$alkyl group or branched $(C_3\text{-}C_6)$alkyl group, such as methyl, ethyl, n-pentyl, n-nonyl, isobutyl, more preferably methyl or ethyl group; the said alkyl group of $R_2$ being not substituted.

According to another embodiment of the disclosure $R_2$ represents a linear $(C_1\text{-}C_{10})$alkyl group or branched $(C_3\text{-}C_{10})$alkyl group, especially a linear $(C_1\text{-}C_6)$alkyl group or branched $(C_3\text{-}C_6)$alkyl group, such as methyl, ethyl, n-pentyl, n-nonyl, isobutyl, more preferably methyl or ethyl; the said alkyl group being substituted by one or more groups selected from i), ii), iii) and iv) as defined herein before. Preferably the said alkyl group being substituted by one or two groups selected from i), ii) and iii), more preferably by one or two groups selected from i) and iii), better substituted by one group iii) as carboxy.

Another variant for radical $R_2$ is that the said alkyl group being substituted by one group iv) especially substituted by one phenyl group.

According to another embodiment of the disclosure $R_2$ represents a $(C_3\text{-}C_8)$cycloalkyl group, preferably a $(C_5\text{-}C_7)$ cycloalkyl group such cyclohexyl.

According to another embodiment of the disclosure $R_2$ represents $C_5\text{-}C_{12}$ aryl group optionally substituted with one or more hydroxyls and/or with one or more $C_1\text{-}C_8$ alkoxy radicals, preferably a phenyl group particularly not substituted.

According to an embodiment $R_3$ represents a hydrogen atom.

According to another embodiment $R_3$ represents a saturated linear $C_1\text{-}C_{10}$ or branched $C_3\text{-}C_{10}$ alkyl group; particularly a linear $(C_1\text{-}C_6)$alkyl group or a branched $(C_3\text{-}C_6)$alkyl group, preferably $(C_1\text{-}C_4)$alkyl group such as methyl group.

Preferably, the compounds of formula (I) and tautomer (I') or their salts, their optical isomers, racemates, and/or solvates such as hydrates and the thereof, alone or as a mixture; have the following meanings:

$R_1$ denotes a radical chosen from:
a) a hydrogen atom;
b) a saturated linear $C_1\text{-}C_6$ or branched $C_3\text{-}C_6$ alkyl group optionally substituted with one or more groups, which may be identical or different, chosen from:
   i) —O—$R_3$
   ii) —S—$R_3$;
   preferably optionally substituted with one or more groups i)
$R_2$ denotes a radical chosen from:
a) a hydrogen atom;
b) a saturated hydrocarbonated group linear $C_1\text{-}C_{10}$ or branched $C_3\text{-}C_{10}$ or cyclic $C_3\text{-}C_8$ such as $C_5\text{-}C_6$, optionally substituted with one or more groups, which may be identical or different, chosen from:
   i) —O—$R_3$
   ii) —SR—$_3$
   iii) —C(O)—O—$R_3$;
   iv) a phenyl group optionally substituted with one or more hydroxyls and/or with one or more $C_1\text{-}C_4$ alkoxy radicals such as methoxy;
   preferably substituted with one or more groups selected from i) and iii), preferably iii) such as carboxy
$R_3$ denotes a radical chosen from:
a) a hydrogen atom;
b) a saturated linear $C_1\text{-}C_6$ or branched $C_3\text{-}C_6$ alkyl group Preferentially, the compounds of formula (I) and tautomer (I') or their salts, their optical isomers, racemates, and/or solvates such as hydrates and the thereof, alone or as a mixture; have the following meanings:

$R_1$ denotes a radical chosen from:
a) a hydrogen atom;
b) a saturated linear $C_1\text{-}C_4$ or branched $C_3\text{-}C_4$ alkyl group optionally substituted with one or more groups, which may be identical or different, chosen from i) —O$R_3$, more preferably not substituted;
$R_2$ denotes a radical chosen from:
a) a hydrogen atom;
b) a saturated hydrocarbonated group linear $C_1\text{-}C_{10}$ or branched $C_3\text{-}C_{10}$ or cyclic $C_3\text{-}C_8$ as C5-C6, optionally substituted with one or more groups, which may be identical or different, chosen from:
   i) —O—$R_3$
   iii) —C(O)—O—$R_3$;
   iv) a $C_5\text{-}C_{12}$ aryl group optionally substituted with one or more hydroxyls and/or with one or more $C_1\text{-}C_4$ alkoxy radicals;
$R_3$ denotes a radical chosen from:
a) a hydrogen atom;
b) a saturated linear $C_1\text{-}C_4$ or branched $C_3\text{-}C_4$ alkyl group such as methyl or ethyl.

Preferentially, the compounds of formula (I) and tautomer (I') or their salts, their optical isomers, racemates, and/or solvates such as hydrates and the thereof, alone or as a mixture;
have the following meanings:
   $R_1$ is a hydrogen atom; and
$R_2$ denotes a radical chosen from:
   a) a hydrogen atom;
   b) a saturated hydrocarbonated group linear $C_1\text{-}C_5$ or branched $C_3\text{-}C_5$ or cyclic $C_3\text{-}C_8$ as C5-C6, substituted with one or more groups, which may be identical or different, chosen from v) —C(O)—O—R3, preferably substituted with one group iii) —C(O)—O—$R_3$;

$R_2$ is even more preferably a saturated hydrocarbonated group linear $C_1$-$C_4$ or branched $C_3$-$C_4$ substituted with one group iii) —C(O)—OR$_3$.

According to another preferred embodiment, compounds of formula (I) and tautomer (I') are selected among compounds of formula (II) and also the tautomers thereof, the salts thereof, the solvates thereof and the optical isomers thereof, and the racemates thereof, alone or as a mixture (II)

-continued (II')

Formula (I) and (I') Wherein R1 and R3 have the same meaning than for compounds of formula (I) and (I') and X denotes an alkylene radical —(CH$_2$)$_n$— with n being an integer ranging inclusively from 1 to 10, preferably ranging from 1 to 6, more preferably ranging from 1 to 4, such as 1, preferably R$_3$ represents a hydrogen atom.

Among the compounds of formula (I), the following compounds are preferably used and their tautomer or their salts, their optical isomers, racemates, and/or solvates such as hydrates and the thereof, alone or as a mixture:

| No. | Structure | Chemical name | CAS No. |
|---|---|---|---|
| 1 | | N-ethyl-2-thioxo-1,2-dihydropyridine-3-carboxamide | 91859-75-5 |
| 2 | | N-methyl-2-thioxo-1,2-dihydropyridine-3-carboxamide | 91859-74-4 |
| 3 | | N-octyl-2-thioxo-1,2-dihydropyridine-3-carboxamide | 91859-77-7 |
| 4 | | N-benzyl-2-thioxo-1,2-dihydropyridine-3-carboxamide | 91859-79-9 |
| 5 | | N-phenyl-2-thioxo-1,2-dihydropyridine-3-carboxamide | 104857-16-1 |
| 6 | | N-cyclohexyl-2-thioxo-1,2-dihydropyridine-3-carboxamide | 91859-78-8 |

-continued

| No. | Structure | Chemical name | CAS No. |
|---|---|---|---|
| 7 | | N-[2-(4-methoxyphenyl)ethyl]-2-thioxo-1,2-dihydropyridine-3-carboxamide | 923682-88-6 |
| 8 | | N-(2-methylpropyl)-2-thioxo-1,2-dihydropyridine-3-carboxamide | 1100027-79-9 |
| 9 | | N-pentyl-2-thioxo-1,2-dihydropyridine-3-carboxamide | 330667-57-7 |
| 10 | | N-nonyl-2-thioxo-1,2-dihydropyridine-3-carboxamide | 1031149-44-6 |
| 11 | | N-(2-hydroxyethyl)-2-thioxo-1,2-dihydropyridine-3-carboxamide | |
| 12 | | N,N-diethyl 2-mercaptonicotinamide | |
| 13 | | N-ethyl-N-(2-hydroxyethyl)-2-thioxo-1,2-dihydropyridine-3-carboxamide | |
| 14 | | N-(2,3-dihydroxypropyl)-2-thioxo-1,2-dihydropyridine-3-carboxamide | |
| 15 | | N-(1,3-dihydroxypropan-2-yl)-2-thioxo-1,2-dihydropyridine-3-carboxamide | |

-continued

| No. | Structure | Chemical name | CAS No. |
|---|---|---|---|
| 16 | | Ethyl N-[(2-thioxo-1,2-dihydropyridin-3-yl)carbonyl]alaninate | |
| 17 | | Ethyl N-[(2-thioxo-1,2-dihydropyridin-3-yl)carbonyl]phenyl alaninate | |
| 18 | | Ethyl N-methyl-N-[(2-thioxo-1,2-dihydropyridin-3-yl)carbonyl]glycinate | |
| 19 | | Ethyl N-[(2-thioxo-1,2-dihydropyridin-3-yl)carbonyl]glycinate | |
| 20 | | N-[(2-thioxo-1,2-dihydropyridin-3-yl)carbonyl]glycine | |
| 21 | | N-methyl-N-[(2-thioxo-1,2-dihydropyridin-3-yl)carbonyl]glycine | |
| 22 | | N,N-bis(2-hydroxyethyl)-2-thioxo-1,2-dihydropyridine-3-carboxamide | |

-continued

| No. | Structure | Chemical name | CAS No. |
|---|---|---|---|
| 23 | | N-(3-methoxypropyl)-2-thioxo-1,2-dihydropyridine-3-carboxamide | |
| 24 | | N-butyl-2-thioxo-1,2-dihydropyridine-3-carboxamide | |

Among these compounds, the following compounds are more particularly preferred:

| No. | Structure | Chemical name | CAS No. |
|---|---|---|---|
| 1 | | N-ethyl-2-thioxo-1,2-dihydropyridine-3-carboxamide | 91859-75-5 |
| 2 | | N-methyl-2-thioxo-1,2-dihydropyridine-3-carboxamide | 91859-74-4 |
| 4 | | N-benzyl-2-thioxo-1,2-dihydropyridine-3-carboxamide | 91859-79-9 |
| 6 | | N-cyclohexyl-2-thioxo-1,2-dihydropyridine-3-carboxamide | 91859-78-8 |
| 7 | | N-[2-(4-methoxyphenyl)ethyl]-2-thioxo-1,2-dihydropyridine-3-carboxamide | 923682-88-6 |
| 9 | | N-pentyl-2-thioxo-1,2-dihydropyridine-3-carboxamide | 330667-57-7 |

-continued

| No. | Structure | Chemical name | CAS No. |
|-----|-----------|---------------|---------|
| 11 | | N-(2-hydroxyethyl)-2-thioxo-1,2-dihydropyridine-3-carboxamide | |
| 12 | | N,N-diethyl 2-mercaptonicotinamide | |
| 14 | | N-(2,3-dihydroxypropyl)-2-thioxo-1,2-dihydropyridine-3-carboxamide | |
| 15 | | N-(1,3-dihydroxypropan-2-yl)-2-thioxo-1,2-dihydropyridine-3-carboxamide | |
| 16 | | Ethyl N-[(2-thioxo-1,2-dihydropyridin-3-yl)carbonyl]alaninate | |
| 17 | | Ethyl N-[(2-thioxo-1,2-dihydropyridin-3-yl)carbonyl]phenyl alaninate | |
| 18 | | Ethyl N-methyl-N-[(2-thioxo-1,2-dihydropyridin-3-yl)carbonyl]glycinate | |

-continued

| No. | Structure | Chemical name | CAS No. |
|---|---|---|---|
| 19 | | Ethyl N-[(2-thioxo-1,2-dihydropyridin-3-yl)carbonyl]glycinate | |
| 20 | | N-[(2-thioxo-1,2-dihydropyridin-3-yl)carbonyl]glycine | |
| 21 | | N-methyl-N-[(2-thioxo-1,2-dihydropyridin-3-yl)carbonyl]glycine | |

More preferably, among these compounds, the following compounds are more particularly preferred:

| No. | Structure | Chemical name | CAS No. |
|---|---|---|---|
| 1 | | N-ethyl-2-thioxo-1,2-dihydropyridine-3-carboxamide | 91859-75-5 |
| 9 | | N-pentyl-2-thioxo-1,2-dihydropyridine-3-carboxamide | 330667-57-7 |
| 16 | | Ethyl N-[(2-thioxo-1,2-dihydropyridin-3-yl)carbonyl]alaninate | |
| 18 | | Ethyl N-methyl-N-[(2-thioxo-1,2-dihydropyridin-3-yl)carbonyl]glycinate | |

-continued

| No. | Structure | Chemical name | CAS No. |
|-----|-----------|---------------|---------|
| 19 | | Ethyl N-[(2-thioxo-1,2-dihydropyridin-3-yl)carbonyl]glycinate | |
| 20 | | N-[(2-thioxo-1,2-dihydropyridin-3-yl)carbonyl]glycine | |
| 21 | | N-methyl-N-[(2-thioxo-1,2-dihydropyridin-3-yl)carbonyl]glycine | |

Even more preferably, among these compounds, the following compounds are more particularly preferred:

| No. | Structure | Chemical name | CAS No. |
|-----|-----------|---------------|---------|
| 18 | | Ethyl N-methyl-N-[(2-thioxo-1,2-dihydropyridin-3-yl)carbonyl]glycinate | |
| 19 | | Ethyl N-[(2-thioxo-1,2-dihydropyridin-3-yl)carbonyl]glycinate | |
| 20 | | N-[(2-thioxo-1,2-dihydropyridin-3-yl)carbonyl]glycine | |
| 21 | | N-methyl-N-[(2-thioxo-1,2-dihydropyridin-3-yl)carbonyl]glycine | |

In a most preferred embodiment, the compound according to the instant disclosure is the following:

N-[(2-thioxo-1,2-dihydropyridin-3-yl)carbonyl]glycine

All compounds can be obtained by chemical method known by man skilled in the art, from commercially available reagents. We can for example use the synthetic method disclosed in the European patent application EP3 390 363.

The composition used according to the disclosure comprises at least one compound of formulae (I) and/or (II) as described above, in a physiologically acceptable medium.

The compound (I), (I'), (II) and/or (II') may be present in the composition used according to the disclosure in an amount which may be between 0.01% and 10% by weight, preferably between 0.1% and 5% by weight, in particular from 0.5% to 3% by weight, relative to the total weight of the composition. UV Boosters Ethylhexylmethoxycrylene and diethylhexyl syringylidenemalonate have been used to boost the SPF of organic UV filtering agents. These compounds, alone or in combinations, boost the SPF of organic UV filtering agent because they act as highly efficient singlet state quenchers. In the instant disclosure, the UV boosters are being used in the photostabilization of the Thiopyridone.
Ethylhexylmethoxycrylene In some instances, Ethylehexyl methoxycrylene is present from about 0.2 to about 3 wt. %, based on the total weight of the cosmetic composition. In various embodiments, Ethylehexyl methoxycrylene is present from about 0.3 to about 2.8 wt. %, based on the total weight of the cosmetic composition. The total amount of the Ethylehexyl methoxycrylene in the compositions may be, for example, from about 0.2 to about 3 wt. %, based on the total weight of the cosmetic composition. In some instance, the total amount of Ethylhexyl methoxycrylene in the compositions may be from about 0.2 wt. % to about 2.9 wt. %, about 2.8 wt. %, about 2.7 wt. %, about 2.6 wt. %, about 2.5 wt. %, about 2.4 wt. %, about 2.3 wt. %, about 2.2 wt. %, about 2.1 wt. %, about 2.0 wt. %, or about 1.8 wt. %. Likewise, in some instances the total amount of Ethylhexyl methoxycrylene in the compositions may be, for example, from about 0.2 to about 2.8 wt. %, about 2.7 wt. %, about 2.6 wt. %, about 2.5 wt. %, about 2.4 wt. %, about 2.3 wt. %, about 2.2 wt. %, about 2.1 wt. %, about 2.0 wt. %, or about 1.8 wt. %. Additionally, the total amount of Ethylhexyl methoxycrylene in the compositions may be from about 0.25 to about 3 wt. %, about 2.9 wt. %, about 2.8 wt. %, about 2.7 wt. %, about 2.6 wt. %, about 2.5 wt. %, about 2.4 wt. %, about 2.3 wt. %, about 2.2 wt. %, about 2.1 wt. %, about 2.0 wt. %, or about 1.8 wt. %. Additionally, the total amount of Ethylhexyl methoxycrylene in the compositions may be about 0.3 to about 3 wt. %, about 2.9 wt. %, about 2.8 wt. %, about 2.7 wt. %, about 2.6 wt. %, about 2.5 wt. %, about 2.4 wt. %, about 2.3 wt. %, about 2.2 wt. %, about 2.1 wt. %, about 2.0 wt. %, or about 1.8 wt. %. Finally, the total amount of Ethylhexyl methoxycrylene in the compositions may be about 0.3 to about 2.9 wt. %, about 0.3 to about 2.8 wt. %, about 0.3 to about 2.7 wt. %, about 0.3 to about 2.6 wt. %, about 0.3 to about 2.5 wt. %, or about 2.4 wt. %.
Diethylhexyl Syringylidenemalonate In some embodiments, Diethyl Syringylidenemalonate is present from about 0.2 to about 3 wt. %, based on the total weight of the cosmetic composition.

In some instances, Diethyl Syringylidenemalonate is present from about 0.2 to about 3 wt. %, based on the total weight of the cosmetic composition. In various embodiments, Diethyl Syringylidenemalonate is present from about 0.3 to about 2.8 wt. %, based on the total weight of the cosmetic composition. The total amount of the Diethyl Syringylidenemalonate in the compositions may be, for example, from about 0.2 to about 3 wt. %, based on the total weight of the cosmetic composition. In some instance, the total amount of Diethyl Syringylidenemalonate in the compositions may be from about 0.2 wt. % to about 2.9 wt. %, about 2.8 wt. %, about 2.7 wt. %, about 2.6 wt. %, about 2.5 wt. %, about 2.4 wt. %, about 2.3 wt. %, about 2.2 wt. %, about 2.1 wt. %, about 2.0 wt. %, or about 1.8 wt. %. Likewise, in some instances the total amount of Diethyl Syringylidenemalonate in the compositions may be, for example, from about 0.2 to about 2.8 wt. %, about 2.7 wt. %, about 2.6 wt. %, about 2.5 wt. %, about 2.4 wt. %, about 2.3 wt. %, about 2.2 wt. %, about 2.1 wt. %, about 2.0 wt. %, or about 1.8 wt. %. Additionally, the total amount of Diethyl Syringylidenemalonate in the compositions may be from about 0.25 to about 3 wt. %, about 2.9 wt. %, about 2.8 wt. %, about 2.7 wt. %, about 2.6 wt. %, about 2.5 wt. %, about 2.4 wt. %, about 2.3 wt. %, about 2.2 wt. %, about 2.1 wt. %, about 2.0 wt. %, or about 1.8 wt. %. Additionally, the total amount of Diethyl Syringylidenemalonate in the compositions may be about 0.3 to about 3 wt. %, about 2.9 wt. %, about 2.8 wt. %, about 2.7 wt. %, about 2.6 wt. %, about 2.5 wt. %, about 2.4 wt. %, about 2.3 wt. %, about 2.2 wt. %, about 2.1 wt. %, about 2.0 wt. %, or about 1.8 wt. %. Finally, the total amount of Diethyl Syringylidenemalonate in the compositions may be about 0.3 to about 2.9 wt. %, about 0.3 to about 2.8 wt. %, about 0.3 to about 2.7 wt. %, about 0.3 to about 2.6 wt. %, about 0.3 to about 2.5 wt. %, or about 2.4 wt. %.

The total amount of UV boosters in the compositions may be, for example, from about 0.2 to about 0.5%, based on the total weight of the cosmetic composition. In some instance, the total amount of UV boosters in the compositions may be, for example, from about 0.2, 0.22, 0.24, 0.26, 0.28, 0.30, 0.32, 0.34 to about 0.34, 0.36, 0.38, 0.40, 0.42, 0.44, 0.46, 0.48, or 0.5 wt. %, based on the total weight of the cosmetic composition.
pH Adjusting Agent The composition according to the present disclosure may comprise at least one pH adjusting agent (pH adjuster). Two or more pH adjusting agents may be used in combination. Thus, a single type of pH adjusting agent or a combination of different types of pH adjusting agents may be used.

As the pH adjusting agent, at least one acidifying agent and/or at least one basifying agent (alkaline agent) may be used.

The acidifying agent may be a monovalent or polyvalent, such as divalent, acid.

The acidifying agents can be, for example, mineral (inorganic) acids such as hydrochloric acid, sulfuric acid, phosphoric acid, or organic acids such as carboxylic acids, for instance tartaric acid, citric acid, and lactic acid, as well as sulphonic acids.

The basifying agent may be a monovalent or polyvalent, such as divalent, base.

The basifying agents may be mineral (inorganic) or organic, or hybrid.

The mineral basifying agents may be chosen from aqueous ammonia; alkali metal carbonates or bicarbonates such as sodium or potassium carbonates and sodium or potassium bicarbonates; alkali metal hydroxides such as sodium hydroxide and potassium hydroxide; and mixtures thereof.

The organic basifying agents may be chosen from organic amines with a pKb at 25° C. of less than 12, preferably less than 10, and even more advantageously less than 6. It should be noted that it is the pKb corresponding to the function of highest basicity. In addition, the organic amines do not comprise any alkyl or alkenyl fatty chains comprising more than ten carbon atoms.

The organic basifying agent may be chosen, for example, from alkanolamines, oxyethylenated and/or oxypropylenated ethylenediamines, amino acids and amine compounds of formula (III) below:

$$R_x \diagdown \underset{R_y \diagup}{N} - W - \underset{\diagdown R_t}{\overset{\diagup R_z}{N}} \tag{III}$$

in which

W represents a $C_1$-$C_6$ divalent alkylene radical optionally substituted with one or more hydroxyl groups or a $C_1$-$C_6$ alkyl radical, and optionally interrupted with one or more heteroatoms such as O and N, and $R_x$, $R_y$, $R_z$, and $R_t$, which may be identical or different, represent a hydrogen atom or a $C_1$-$C_6$ alkyl, $C_1$-$C_6$ hydroxyalkyl, or $C_1$-$C_6$ aminoalkyl radical.

Examples of the amine compounds of formula (III) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising one to three identical or different $C_1$-$C_4$ hydroxyalkyl radicals may be suitable for the present disclosure. Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

Amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present disclosure, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

It may be preferable that the amino acids are basic amino acids comprising an additional amine function optionally included in a ring or in an ureido function.

Such basic amino acids may preferably be chosen from those corresponding to formula (IV) below:

$$R - CH_2 - \underset{\diagdown CO_2H}{\overset{\diagup NH_2}{CH}} \tag{IV}$$

in which

R represents a group chosen from:

(imidazole ring structure with NH)

$-(CH_2)_3-NH_2$, $-(CH_2)_2-NH_2$, $-(CH_2)_2-NH-CO-NH_2$, and $$-(CH_2)_2NH - \underset{\overset{\|}{NH}}{C} - NH_2.$$

The compounds corresponding to formula (IV) include histidine, lysine, arginine, ornithine and citrulline.

The organic basifying agent may be chosen from organic amines of heterocyclic type. Besides histidine that has already been mentioned in the amino acids, mention may in particular be made of pyridine, piperidine, imidazole, triazole, tetrazole and benzimidazole.

The organic basifying agent may also be chosen from amino acid dipeptides. As amino acid dipeptides that may be used in the present disclosure, mention may be made especially of camosine, anserine and baleine.

The organic basifying agent may also be chosen from compounds comprising a guanidine function. As amines of this type that may be used in the present disclosure, besides arginine, which has already been mentioned as an amino acid, mention may be made especially of creatine, creatinine, 1,1-dimethylguanidine, 1,1-diethyl-guanidine, glycocyamine, metformin, agmatine, N-amidinoalanine, 3-guanidino-propionic acid, 4-guanidinobutyric acid and 2-([amino(imino)methyl]amino)ethane-1-sulfonic acid.

In a preferred embodiment of the present disclosure, the organic basifying agent may be selected from amino acids, preferably basic amino acids, and more preferably arginine, lysine, histidine or mixtures thereof. Even more preferentially, the organic basifying agent may be arginine.

Hybrid compounds that may be mentioned include the salts of the amines mentioned previously with acids such as carbonic acid or hydrochloric acid. Guanidine carbonate or monoethanolamine hydrochloride may be used in particular.

The pH adjusting agent may be present in an amount of 0.01% by weight or more, preferably 0.05% by weight or more, and more preferably 0.1% by weight or more, relative to the total weight of the composition.

The pH adjusting agent may be present in an amount of 15% by weight or less, preferably 10% by weight or less, and more preferably 5% by weight or less, relative to the total weight of the composition.

The pH adjusting agent may be present in an amount ranging from 0.01% to 15% by weight, preferably from 0.05% to 10% by weight, and more preferably from 0.1% to 5% by weight or less, relative to the total weight of the composition.

It is preferable that the composition according to the present disclosure have a pH of 4.5 or more, and more preferably 5 or more.

It is preferable that the composition according to the present disclosure have a pH of 6.5 or less, and more preferably 6 or less.

It is preferable that the composition according to the present disclosure have a pH of from 4.5 to 6.5, and more preferably from 5 to 6.

The pH of the composition means the pH of the aqueous phase of the composition according to the present disclosure.

It may be preferable that at least one buffer or buffering agent also be used, as the pH adjusting agent, in combination with the acidifying agent and/or the basifying agent, in order to stabilize the pH of the composition according to the present disclosure.

As the buffer, any of commonly known buffers may be used. For example, salts of acids or bases, preferably salts of weak acids or weak bases, may be used. For example, sodium citrate or sodium lactate may be used as the buffer, if citric acid or lactic acid is used as the acidifying agent.

Cosmetically Acceptable Carrier System

The cosmetic compositions include a cosmetically acceptable carrier system. The term "cosmetically acceptable" means a carrier that is compatible with any keratinous substrate, and for purposes hereof, includes water and optionally water based solvents subject to any exclusions as disclosed herein.

The cosmetic compositions may comprise any constituent normally employed in the topical application and administration envisaged. Mention may in particular be made of water, solvents, polyols, fatty compounds (i.e. described by the International Federation Societies of Cosmetic Chemists, for example, in Cosmetic Raw Material Analysis and Quality, Volume I: Hydrocarbons, Glycerides, Waxes and Other Esters (Redwood Books, 1994), which is incorporated herein by reference in its entirety), pigments, fillers, silicones, surfactants, thickeners, gelling agents, preservatives and their mixtures in all proportions.

Methods of Use

The instant disclosure also relates to methods of using the cosmetic compositions described herein. For example, the cosmetic compositions can be used in a method that comprises applying the cosmetic compositions to the skin of humans. In some cases, the composition is applied to the face. Furthermore, the cosmetic composition can be used in methods for depigmenting, lightening and/or bleaching keratin materials, preferably skin, comprising the step of: applying to the keratin substance the composition according to the compositions described herein The aforementioned methods are non-therapeutic.

The cosmetic composition may be applied once per day, twice per day, or more than once or twice per day. In some cases, the composition is applied in the evenings before bed. In other cases, the compositions are applied in the morning. In still other cases, the composition may be applied immediately after washing the skin. The compositions may be used once, or for a series of days, weeks, or months. For example, the compositions may be used daily for a period of 1, 2, 3, 4, 5, 6, 7, 8 or more weeks, or months.

The instant disclosure also relates to non-therapeutic cosmetic process for depigmenting, lightening and/or bleaching keratin materials, preferably skin, comprising the step of: applying to the keratin substance the compositions described herein.

These and other aspects of the disclosure are set out in the appended claims and described in greater detail in the detailed description of the disclosure.

This disclosure describes exemplary embodiments in accordance with the general inventive concepts and is not intended to limit the scope of the disclosure in any way. Indeed, the disclosure as described in the specification is broader than and unlimited by the exemplary embodiments set forth herein, and the terms used herein have their full ordinary meaning.

EXAMPLES

Implementation of the present disclosure is provided by way of the following examples. The following examples serve to elucidate aspects of the technology without being limiting in nature.

Example 1

Example 1: Synthesis of compound 20

Compound 20 is synthesized as disclosed in example 2 of patent EP3 390 363.

Example 2

(Inventive Compositions)

The inventive and comparative compositions were prepared using the following general procedure:

The water soluble raw materials were added to the main kettle and dissolved. Polymers were then added and mixed until well-dispersed. Batch was heated to 75° C. In a side kettle, the fatty compounds, silicones, emulsifiers and/or boosters were mixed together and heated to 75° C. The side kettle was added to the main kettle while homogenizing well. When well emulsified, the batch was cooled to room temperature, and actives and fillers were added.

TABLE 1

| | Inventive Compositions | | | | |
| INCI US | Inventive Example 1 | Inventive Example 2 | Inventive Example 3 | Inventive Example 4 | Inventive Example 5 |
| --- | --- | --- | --- | --- | --- |
| Compound of thiopyridinone type | 0.5 | 0.5 | 0.5 | 0.5 | 0.5 |
| Ethylhexyl Methoxycrylene | 1.0 | 1.0 | 0 | 1.0 | 3.0 |

TABLE 1-continued

| | Inventive Compositions | | | | |
|---|---|---|---|---|---|
| INCI US | Inventive Example 1 | Inventive Example 2 | Inventive Example 3 | Inventive Example 4 | Inventive Example 5 |
| Diethylhexyl Syringylidenemalonate | 0.9 | 0.9 | 0.9 | 1.8 | 0 |
| Fatty Compounds | 7.5 | 4.3 | 7.7 | 4.3 | 4.3 |
| Filler | 0.4 | 1.0 | 0.4 | 0 | 0 |
| Polymer | 1.6 | 1.6 | 1.6 | 1.6 | 1.6 |
| Preservative | 0.6 | 0.6 | 0.6 | 0.6 | 0.6 |
| Silicon | 4.6 | 4.6 | 6.1 | 4.6 | 4.6 |
| Solvent | 7.0 | 9.0 | 7.0 | 9.0 | 9.0 |
| Surfactant | 8.7 | 8.7 | 8.7 | 8.7 | 8.7 |
| Active Compound | 1.8 | 1.4 | 1.8 | 1.7 | 1.7 |
| Vitamin | 10.3 | 10.3 | 10.3 | 10.3 | 10.3 |
| Water | Q.S. | Q.S. | Q.S. | Q.S. | Q.S. |

TABLE 2

| | Comparative Compositions | |
|---|---|---|
| INCI US | Comp. Ex. 1 | Comp. Ex. 2 |
| Compound of thiopyridinone type | 0.5 | 0.5 |
| Ethylhexyl Methoxycrylene | 0 | 0 |
| Diethylhexyl Syringylidenemalonate | 0 | 0 |
| Butyl Methoxydibenzoylmethane | 0 | 0 |
| Ethylhexyl Salicylate | 0 | 0 |
| Terephthalylidene Dicamphor Sulfonic Acid | 0 | 0 |
| Octocrylene | 0 | 0 |
| Homosalate | 0 | 0 |
| Mineral Sun Filter | 0 | 0 |
| Fatty Compounds | 3.0 | 7.7 |
| Filler | 0.5 | 0.4 |
| Polymer | 1.5 | 1.6 |
| Preservative | 0.6 | 0.6 |
| Silicon | 1.5 | 6.1 |
| Solvent | 20.3 | 4.0 |
| Surfactant | 2.7 | 8.7 |
| Active Compound | 5.6 | 1.8 |
| Vitamin | 6.0 | 10.3 |
| Water | Q.S. | Q.S. |

Example 3

Inventive Examples 1 and several comparative Examples were tested for photostability. The photostability of the inventive and comparative Examples was assessed by following the procedure described below.

First, the amount of Compound of thiopyridinone type (THP) in formula is metered via HPLC/UV. A specific amount of formula is evenly spread on a PMMA plate to yield a layer of about 2 mg/cm2 (n=4 plates). All plates are exposed to UVA light until a dose of 5 J/cm2, corresponding to daily average UV dose, is reached using a solar simulator instrument. Plates are removed, and solvent is used to wash off the formula film and the Compound of thiopyridinone type is then extracted. This extract is then metered for Compound of thiopyridinone type concentration using HPLC/UV. The photostability % is given as: % Compound of thiopyridinone type after UVA exposure/% Compound of thiopyridinone type initial×100.

The results are presented in Table 3 below.

TABLE 3

| | Photostability Results | | | |
|---|---|---|---|---|
| Examples | % THP*** remaining after UV test | UV Filters (%) | Inventive Booster Mix** (%) | |
| Comp. Ex. 1 | 6% | 0% | 0% | Baseline worst case (no filters or boosters) |
| Comp. Ex. 2 | 63% | 0% | 0% | Better stability than Comp. Ex. 1; but still can be improved. |
| Inventive Ex. 1 | 81% | 0% | 1%-Ethylhexyl Methoxycrylene + 1% Diethylhexyl Syringylidenemalonate | Inventive; not OTC*, and better stability |
| Inventive Ex. 2 | 87% | 0% | 1% Diethylhexyl Syringylidenemalonate | Inventive; not OTC*, and better stability |
| Inventive Ex. 3 | 90% | 0% | 1%-Ethylhexyl Methoxycrylene + 2% Diethylhexyl Syringylidenemalonate | Inventive; not OTC*, and better stability |
| Inventive Ex. 4 | 86% | 0% | 3% Ethylhexyl Methoxycrylene | Inventive; not OTC*, and better stability |

The photostability of Compound of thiopyridinone type formulations containing UV boosters were assessed using the photostability protocol described above.

It was observed that the composition containing the boosters displayed on par or better photostability of the Compound of thiopyridinone type.

It was shown that the Compound of thiopyridinone type was stabilized when the compositions contained one or two boosters such as Ethylhexyl Methoxycrylene and Diethylhexyl Syringylidenemalonate The inventors discovered how the stability of Compound of thiopyridinone type when exposed to light by incorporating one booster or a booster mixed such as Ethylhexyl Methoxycrylene and Diethylhexyl Syringylidenemalonate.

While the disclosure has been described with reference to described embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The term "INCI" is an abbreviation of International Nomenclature of Cosmetic Ingredients, which is a system of names provided by the International Nomenclature Committee of the Personal Care Products Council to describe personal care ingredients.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the disclosure, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

The terms "weight percent" and "wt %" may be used interchangeably and mean percent by weight, based on the total weight of a composition, article or material, except as may be specified with respect to, for example, a phase, or a system that is a component of a composition, article or material. All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic composition comprising:
i) at least one thiopyridinone compound selected from a compound of formula (I) and a compound of formula (I'), or a salt, optical isomer, racemate, or solvate thereof, and mixtures thereof:

(I)

-continued (I')

wherein:

R$_1$ is selected from:

a hydrogen atom; or a linear C$_1$-C$_{10}$ alkyl group or a branched C$_3$-C$_{10}$ alkyl group, each of which is optionally substituted with one or more groups independently selected from —OR$_3$ and —SR$_3$;

R$_2$ is selected from:

a hydrogen atom;

a linear C$_1$-C$_{12}$ alkyl group, a branched C$_3$-C$_{12}$ alkyl group, or a C$_3$-C$_8$ cycloalkyl group, each of which is optionally substituted with one or more groups independently selected from —OR$_3$, —SR$_3$, —C(O)OR$_3$, and a C$_5$-C$_{12}$ aryl group optionally substituted with one or more groups independently selected from OH and C$_1$-C$_8$ alkoxy; or a C$_5$-C$_{12}$ aryl group optionally substituted with one or more groups independently selected from OH and C$_1$-C$_8$ alkoxy;

R$_3$ is selected from:

a hydrogen atom; or a linear C$_1$-C$_{10}$ alkyl group or a branched C$_3$-C$_{10}$ alkyl group;

ii) one or more UV boosters selected from the group consisting of ethylhexyl methoxycrylene, diethyl syringylidenemalonate, and mixtures thereof, and iii) 0 wt. % UV filters;

wherein the weight percentages are based on the total weight of the cosmetic composition; and wherein the association of the one or more UV boosters improves the photostability of the at least one thiopyridinone compound.

2. The composition of claim 1, wherein R$_1$ is a hydrogen atom, a linear C$_1$-C$_{10}$ alkyl group, or a branched C$_3$-C$_{10}$ alkyl group.

3. The composition of claim 1, wherein R$_2$ is a hydrogen atom, a linear C$_1$-C$_{10}$ alkyl group, or a branched C$_3$-C$_{10}$ alkyl group.

4. The composition of claim 1, wherein R$_2$ is a linear C$_1$-C$_{10}$ alkyl group, or a branched C$_3$-C$_{10}$ alkyl group.

5. The composition of claim 1, wherein R$_2$ is a C$_3$-C$_8$ cycloalkyl group or a C$_5$-C$_{12}$ aryl group optionally substituted with one or more groups independently selected from OH and C$_1$-C$_8$ alkoxy.

6. The composition of claim 1, wherein:

R$_1$ is selected from:

a hydrogen atom; or a linear C$_1$-C$_6$ alkyl group or a branched C$_3$-C$_6$ alkyl group, each of which is optionally substituted with one or more groups independently selected from —OR$_3$ and —SR$_3$;

R$_2$ is selected from:

a hydrogen atom;

a linear C$_1$-C$_{10}$ alkyl group, a branched C$_3$-C$_{10}$ alkyl group, or a C$_3$-C$_8$ cycloalkyl group, each of which is optionally substituted with one or more groups independently selected from —OR$_3$, —SR$_3$, —C(O)OR$_3$, and a phenyl group optionally substituted with one or more groups independently selected from OH and C$_1$-C$_8$ alkoxy; and R$_3$ is selected from:

a hydrogen atom; or a linear C$_1$-C$_6$ alkyl group or a branched C$_3$-C$_6$ alkyl group.

7. The composition of claim 1, wherein the one or more thiopyridinone compounds of formula (I) and formula (I') are selected from the group consisting of compounds 1 to 24, or a salt, optical isomer, racemate, or solvate thereof, and mixtures thereof

| No. | Structure | Chemical name |
|---|---|---|
| 1 | | N-ethyl-2-thioxo-1,2-dihydropyridine-3-carboxamide |
| 2 | | N-methyl-2-thioxo-1,2-dihydropyridine-3-carboxamide |
| 3 | | N-octyl-2-thioxo-1,2-dihydropyridine-3-carboxamide |

-continued

| No. | Structure | Chemical name |
| --- | --- | --- |
| 4 | | N-benzyl-2-thioxo-1,2-dihydropyridine-3-carboxamide |
| 5 | | N-phenyl-2-thioxo-1,2-dihydropyridine-3-carboxamide |
| 6 | | N-cyclohexyl-2-thioxo-1,2-dihydropyridine-3-carboxamide |
| 7 | | N-[2-(4-methoxyphenyl)ethyl]-2-thioxo-1,2-dihydropyridine-3-carboxamide |
| 8 | | N-(2-methylpropyl)-2-thioxo-1,2-dihydropyridine-3-carboxamide |
| 9 | | N-pentyl-2-thioxo-1,2-dihydropyridine-3-carboxamide |
| 10 | | N-nonyl-2-thioxo-1,2-dihydropyridine-3-carboxamide |
| 11 | | N-(2-hydroxyethyl)-2-thioxo-1,2-dihydropyridine-3-carboxamide |
| 12 | | N,N-diethyl 2-mercaptonicotinamide |

-continued

| No. | Structure | Chemical name |
|---|---|---|
| 13 | | N-ethyl-N-(2-hydroxyethyl)-2-thioxo-1,2-dihydropyridine-3-carboxamide |
| 14 | | N-(2,3-dihydroxypropyl)-2-thioxo-1,2-dihydropyridine-3-carboxamide |
| 15 | | N-(1,3-dihydroxypropan-2-yl)-2-thioxo-1,2-dihydropyridine-3-carboxamide |
| 16 | | Ethyl N-[(2-thioxo-1,2-dihydropyridin-3-yl)carbonyl]alaninate |
| 17 | | Ethyl N-[(2-thioxo-1,2-dihydropyridin-3-yl)carbonyl]phenyl alaninate |
| 18 | | Ethyl N-methyl-N-[(2-thioxo-1,2-dihydropyridin-3-yl)carbonyl]glycinate |
| 19 | | Ethyl N-[(2-thioxo-1,2-dihydropyridin-3-yl)carbonyl]glycinate |

-continued

| No. | Structure | Chemical name |
|-----|-----------|---------------|
| 20 | | N-[(2-thioxo-1,2-dihydropyridin-3-yl)carbonyl]glycine |
| 21 | | N-methyl-N-[(2-thioxo-1,2-dihydropyridin-3-yl)carbonyl]glycine |
| 22 | | N,N-bis(2-hydroxyethyl)-2-thioxo-1,2-dihydropyridine-3-carboxamide |
| 23 | | N-(3-methoxypropyl)-2-thioxo-1,2-dihydropyridine-3-carboxamide |
| 24 | | N-butyl-2-thioxo-1,2-dihydropyridine-3-carboxamide. |

8. The composition of claim 1, wherein the one or more UV boosters are present in an amount ranging from about 0.01 to about 10 wt. %, based on the total weight of the cosmetic composition.

9. The composition of claim 1, wherein compound i) is present in an amount ranging from about 0.01 to about 10 wt. %, based on the total weight of the cosmetic composition.

10. The composition of claim 1, wherein ethylhexyl methoxycrylene is present in an amount ranging from about 0.2 to about 3 wt. %, based on the total weight of the cosmetic composition.

11. The composition of claim 1, wherein diethyl syringylidenemalonate is present in an amount ranging from about 0.2 to about 3 wt. %, based on the total weight of the cosmetic composition.

12. The composition of claim 1, wherein the pH is from about 4.5 to about 6.5.

13. A cosmetic composition comprising:

i) from about 0.01 to about 10 wt. % of at least one thiopyridinone compound selected from a compound of formula (I) and a compound of formula (I'), or an optical isomer, racemate, or solvate thereof, and mixtures thereof:

(I)

(I')

wherein:

$R_1$ is selected from:

a hydrogen atom; or a linear $C_1$-$C_{10}$ alkyl group or a branched $C_3$-$C_{10}$ alkyl group, each of which is optionally substituted with one or more groups independently selected from —$OR_3$ and —$SR_3$;

$R_2$ is selected from:

a hydrogen atom;

a linear $C_1$-$C_{12}$ alkyl group, a branched $C_3$-$C_{12}$ alkyl group, or a $C_3$-$C_8$ cycloalkyl group, each of which is optionally substituted with one or more groups independently selected from —$OR_3$, —$SR_3$, —$C(O)OR_3$, and a $C_5$-$C_{12}$ aryl group optionally substituted with one or more groups independently selected from OH and $C_1$-$C_8$ alkoxy; or a $C_5$-$C_{12}$ aryl group optionally substituted with one or more groups independently selected from OH and $C_1$-$C_8$ alkoxy;

$R_3$ is selected from:

a hydrogen atom; or a linear $C_1$-$C_{10}$ alkyl group or a branched $C_3$-$C_{10}$ alkyl group;

ii) from about 0.2 to about 4.8 wt. % of one or more UV boosters selected from the group consisting of ethylhexyl methoxycrylene, diethyl syringylidenemalonate, and mixtures thereof, and iii) 0 wt. % UV filters;

wherein the weight percentages are based on the total weight of the cosmetic composition; and wherein the association of the one or more UV boosters improves the photostability of the at least one thiopyridinone compound.

14. The composition of claim 1 wherein one or more compounds of formula (I) is compound 20:

20

N-[(2-thioxo-1,2-dihydropyridin-3-yl)carbonyl]glycine

\* \* \* \* \*